United States Patent
Shaffer et al.

(10) Patent No.: US 9,017,717 B2
(45) Date of Patent: Apr. 28, 2015

(54) BANDAGE FOR FACILITATING TRANSDERMAL RESPIRATION AND HEALING

(75) Inventors: Thomas H. Shaffer, Chadds Ford, PA (US); Robert G. Stern, Tucson, AZ (US); Marla R. Wolfson, Wyndmoor, PA (US)

(73) Assignee: Peach Technologies LLC, Philadelphia, PA (US)

( * ) Notice: Subject to any disclaimer, the term of this patent is extended or adjusted under 35 U.S.C. 154(b) by 2848 days.

(21) Appl. No.: 11/278,885

(22) Filed: Apr. 6, 2006

(65) Prior Publication Data

US 2007/0166357 A1    Jul. 19, 2007

Related U.S. Application Data

(60) Provisional application No. 60/743,129, filed on Jan. 16, 2006.

(51) Int. Cl.
| | |
|---|---|
| A61F 13/00 | (2006.01) |
| A61K 9/70 | (2006.01) |
| A61L 15/00 | (2006.01) |
| A61L 15/16 | (2006.01) |
| A61L 15/20 | (2006.01) |
| A61L 15/44 | (2006.01) |

(52) U.S. Cl.
CPC .......... *A61K 9/7084* (2013.01); *A61F 13/00063* (2013.01); *A61F 2013/00246* (2013.01); *A61F 2013/00855* (2013.01); *A61L 15/20* (2013.01); *A61L 15/44* (2013.01); *A61L 2300/10* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 4,366,169 A | * 12/1982 | White | 514/755 |
| 4,661,105 A | 4/1987 | Gale | |
| 5,556,375 A | * 9/1996 | Ewall | 602/58 |
| 5,964,721 A | * 10/1999 | Augustine | 602/2 |
| 6,113,922 A | * 9/2000 | Swenson et al. | 424/400 |
| 6,126,721 A | 10/2000 | Nemser et al. | |
| 6,368,592 B1 | 4/2002 | Colton et al. | |
| 6,488,958 B1 | 12/2002 | Himmelsbach et al. | |
| 6,726,840 B1 | 4/2004 | Arcella et al. | |
| 6,746,689 B2 | 6/2004 | Fischer et al. | |
| 6,818,226 B2 | 11/2004 | Reed et al. | |
| 6,865,825 B2 | 3/2005 | Bailey, Sr. et al. | |
| 6,916,487 B2 | 7/2005 | Klose et al. | |
| 7,001,613 B2 | 2/2006 | Radloff et al. | |
| 7,014,630 B2 | * 3/2006 | Rosati | 604/304 |
| 7,160,553 B2 | * 1/2007 | Gibbins et al. | 424/449 |

OTHER PUBLICATIONS

Stephens et al. "Effect of changes in inspired oxygen and carbon dioxide tension on wound tensile strength", Annals of Surgery, Apr. 1971, vol. 173, No. 4, pp. 515-519.*
U. Kaisers, K. P. Kelly and T. Busch Liquid Ventilation British Journal of Anaesthesia 91 (1): 143-51 (2003).

* cited by examiner

*Primary Examiner* — Isis Ghali
(74) *Attorney, Agent, or Firm* — Paul & Paul

(57) ABSTRACT

A bandage includes a reservoir filled with a perfluorochemical fluid, saturated with oxygen. Oxygen passes through a permeable membrane to the skin or wound to promote healing, and carbon dioxide travels from the skin or wound to the reservoir.

16 Claims, 1 Drawing Sheet

BANDAGE FOR FACILITATING TRANSDERMAL RESPIRATION AND HEALING

BACKGROUND OF THE INVENTION

1. Field of the Invention

The present invention relates to medical bandages.

2. Brief Description of the Prior Art

A fundamental concept in the healing of skin, promoting skin health, and healing tissue injuries is the delivery of adequate oxygenation, carbon dioxide removal, and blood flow to affected areas. A variety of basic methodologies are commonly applied in both the medical and physical therapy disciplines to promote such healing. These include revascularization to areas with interrupted blood flow (via surgical bypass or endovascular therapy), drug therapy, and local warming (via direct heat application or ultrasound) to increase local perfusion and improve oxygen delivery and carbon dioxide removal.

Alternatively, hyperbaric therapy has been utilized for direct delivery of oxygen at the tissue site via a pressurized, oxygenated environment to treat wounds.

Perfluorochemical (PFC) liquids have been utilized to deliver oxygen systemically via the lungs and as an artificial blood substitute. In addition, the anti-inflammatory nature of PFC liquids and vapors when used in cell and in vivo conditions has been demonstrated. In one case a fluorocarbon liquid has been used in a bath environment to partially treat foot ulcers.

Wounds and tissue injuries constitute a very large grouping of medical conditions including ischemic/decubitus ulcers, traumatic injuries, thermal injuries, reconstructive and/or cosmetic procedures of poorly vascularized regions of vascularly compromised patients, and mechanical musculoskeletal injuries, including but not limited to skin, muscle, cartilage, ligament, and tendon injuries. A wide variety of skin disorders including but not limited to psoriasis, atopic dermatitis, skin infections including bacterial, fungal, and viral diseases, and post viral processes such as shingles, can also be included in this group. While it is difficult to quantify all the skin diseases, ulcers, burns, sprains, and other injuries that occur in the population, it is safe to assume that this occurs in many millions of patients in the United States. For example, in a Canadian study, 1.8% of the population was determined to have open or healed ulcers of the lower extremity. Extrapolation of this data results in an estimated 5.3 million such patients in the United States alone, which is likely to be conservative given the considerably higher rate of diabetes and peripheral vascular disease in the United States. Similarly, in an older literature review from 1987, over a million people per year seek medical attention each year in the United States for ankle sprains alone, which is presumably exceedingly conservative given the growth of exercise in the youth and adult population as well as the preponderance of patients who do not seek physician attention for their less significant injuries.

Adding the number of skin diseases, burn injuries, traumatic and other wounds, reconstructive and cosmetic surgical challenges, and tissue injuries yields estimates in the tens of millions of wound and tissue injury patients in the United States alone each year.

There is a continuing need to provide treatment for these diseases, injuries and conditions.

SUMMARY OF THE INVENTION

The present invention provides a treatment process to promote skin health, skin healing, and tissue healing, as well as to promote musculoskeletal fatigue recovery.

The present process comprises applying to the skin of an animal, such as a mammal, and in particular, to the skin of a human being, a bandage comprising a reservoir containing perfluorochemical fluid. The reservoir is sealed with a gas-permeable membrane.

In one aspect of the present invention, gas-permeable membrane is permeable to carbon dioxide, and the perfluorochemical fluid contains less than a predetermined amount of carbon dioxide dissolved in the perfluorochemical fluid. Preferably, the predetermined amount of carbon dioxide dissolved in the perfluorochemical fluid has a maximum partial pressure of 45 mm Hg. More preferably, the predetermined amount of carbon dioxide dissolved in the perfluorochemical fluid is less than 0.1 mm Hg. In this aspect, the bandage is preferably sealed to the environment until application of the bandage to prevent premature uptake of carbon dioxide from the environment, and the process additionally comprises removing the seal from the bandage before applying the bandage to the skin.

In another aspect of the present invention, the perfluorochemical fluid preferably has at least one gaseous material dissolved therein, and the membrane is permeable to at least one gaseous material.

The present process further preferably comprises maintaining contact between the bandage and the skin for a predetermined period of time.

In one presently preferred embodiment, the permeability of the membrane to the gaseous material increases as a function of temperature, so that contact with the skin raises the temperature of the membrane, and enhances the transfer of the gaseous material through the membrane to the skin.

In one particularly preferred embodiment of the present invention the gaseous material is oxygen. In this case, the bandage preferably further comprises an oxygen-impermeable cover, and the reservoir is sealed between the cover and the membrane. Preferably, the membrane is permeable to carbon dioxide, so that carbon dioxide can diffuse from the skin or wound through the membrane, and dissolve in the perfluorochemical fluid of the reservoir.

Preferably, the perfluorochemical fluid is selected from the group consisting of $C_4F_9CH=CH_4C_9$, i-$C_3F_9CH=CHC_6F_{13}$, $C_6F_{13}CH=CHC_6F_{13}$, $C_{10}F_{18}$, $C_8F_{17}Br$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicycio[3,3,1]nonane, F-trimethylbicyclo[3,3,1]nonane, F-tripropylamine, F-tributylamine, C-4 alkyl decalin $C_{14}F_{24}/C_{14}F_{26}$, $C_{10}F_{18}$, $C_8F_{17}Br$, $C_6F_{14}$-perfluorohexanes, FC-77, and mixtures thereof. Preferably, the perfluorochemical fluid comprises at least one fluorinated hydrocarbon having at least one-half of the corresponding hydrocarbon's hydrogen atoms substituted by fluorine.

In another aspect of the present invention, a medicament is also included in the reservoir. Preferably, in this case the medicament is selected from the group consisting of tissue growth promoters, hormones, antibiotics, genetic delivery systems, and pharmaceutical delivery systems.

In yet another aspect, the present invention further provides for dissolving other therapeutic gases in the perfluorochemical fluid to enhance the oxygenation of the perfluorochemical fluid. In this case, it is preferred that the other gases be selected from the group consisting of helium and nitric oxide.

DETAILED DESCRIPTION

Figure 1:
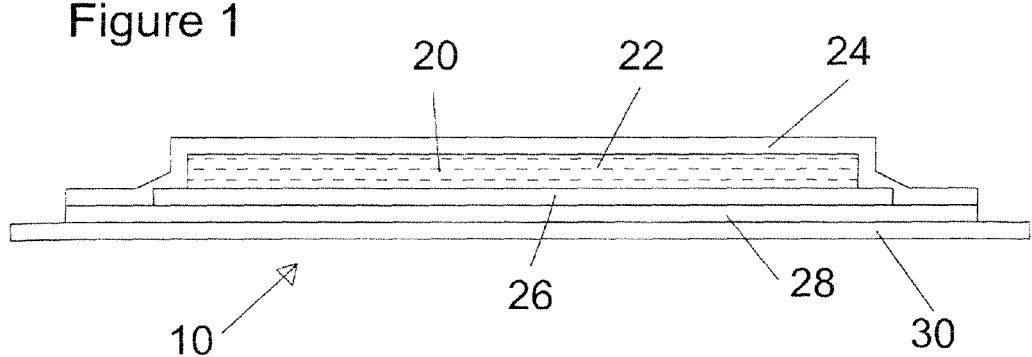
FIG. 1 is a longitudinal cross-sectional view of a bandage according to the present invention taken along the line 1-1 of FIG. 2.
Figure 2:
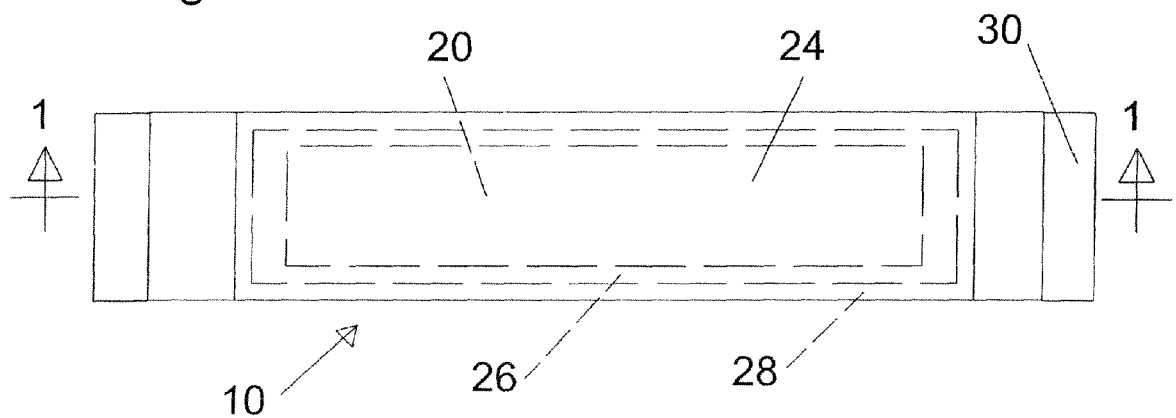
FIG. 2 is a top plan view of the bandage of FIG. 1.

Referring now to the drawings, in which like reference numerals designate like elements in each of the several views, there is shown in FIG. 1 a longitudinal cross-sectional view of a bandage 10 according to the present invention. The bandage 10 includes an internal reservoir 20 having a top, a bottom and four sides, for containing a perfluorochemical fluid saturated with dissolved oxygen. The perfluorochemical fluid preferably is both saturated with dissolved oxygen and contains as little dissolved carbon dioxide as practical. A mechanical support structure 22 formed from gauze or another nonwoven material is disposed inside the reservoir 20. As can be seen in the top plan view of FIG. 2 taken with the cross-sectional view of FIG. 1, the reservoir 20 is sealed on top and on all four sides by a generally rectangular cover 24. The bottom of the reservoir 20 is sealed with a membrane 26 that is permeable to the oxygen that is dissolved in the perfluorochemical fluid, but otherwise retains the contents of the reservoir 20 within the reservoir 20. The membrane 26 is also permeable to carbon dioxide, so that carbon dioxide can diffuse from the skin or wound to which the bandage 10 is applied and dissolve in the perfluorocarbon fluid in the reservoir 20. The bottom of the membrane 26 may or may not be coated with a layer of adhesive 28 for securing the bandage 10 to the skin, depending upon the specific clinical application. If an adhesive is used, an adhesive highly permeable to both oxygen and carbon dioxide is preferably selected. A piece of release material 30 covers the bottom of the adhesive layer 28 to protect the adhesive layer from inadvertent contact, enabling a user to remove the release material 30 immediately before applying the bandage 10 to the skin. While the reservoir 20 has been illustrated with a generally rectangular shape, the reservoir 20 can alternatively be provided in another shape, such as round or oval.

In this embodiment, the reservoir 20 conforms to the rectangular or oval/round shape normally associated with gauze component of a conventional bandage strip. However, the bandage 10 of the present invention would serve as an active oxygenator of wounds wherever placed. Given the nature of perfluorochemical fluids, the bandage 10 also serves to remove carbon dioxide and other gases that are emitted by wounds and normal skin, given the high solubility of most gases in perfluorochemical fluids.

In general, both carbon dioxide and oxygen are highly soluble in perfluorochemical fluids, with carbon dioxide typically being about three to four times as soluble as oxygen. U. Kaisers et al., "Liquid Ventilation," *British J. Anesthesia*, 91 (1): 143-151 (2003).

While a bandage assuming the shape of a conventional rectangular Band-Aid™ has been illustrated, the bandage of the present invention can be provided in other shapes and forms, depending on the location on the body to which the bandage is intended for application. For example, the bandage can take the form of an elastic wrap placed around a specific body part to modulate surface contact and application pressure, with the reservoir incorporated into the bandage wrap and directly applied to skin and held in place by the elastic bandage, with the membrane directly opposed to the skin. In such embodiments it may be desirable to omit an adhesive layer.

In addition, a bandage according to the present invention can be provided in the form of a contour-formed and/or custom-fit article in which the reservoir is either rigid or conformable in shape, and intended for a specific body part. For example, the bandage of the present invention can take the form of a pre-shaped face-mask, buttocks area of the ilial tuberosities, or a glove intended to be worn on the hand, a sock intended to be worn on the foot, or the like, with the membrane being positioned in the bandage so that membrane will be applied directly to a predetermined target area of the skin or tissue.

Thus, the reservoir (with the optional adhesive coating) can be applied directly to skin or open wounds with gas exchange, including but not limited to oxygenation and carbon dioxide removal, occurring directly into the area of direct contact via the membrane.

The permeable membrane is preferably sealed with a gas impermeable peel away-type cover to prevent gas loss, undesired gas uptake, or leakage until time of application.

In one aspect of the present invention, gas-permeable membrane is permeable to carbon dioxide, and the perfluorochemical fluid contains less than a predetermined amount of carbon dioxide dissolved in the perfluorochemical fluid. Given the high solubility of carbon dioxide in perfluorochemical fluids, the bandage thus functions to remove carbon dioxide from the site on the skin or wound to which the bandage is applied. Preferably, the predetermined amount of carbon dioxide dissolved in the perfluorochemical fluid has a partial pressure of 45 mm Hg, approximately the maximum amount found in blood circulating in mammals. More preferably, the predetermined amount of carbon dioxide dissolved in the perfluorochemical fluid has a partial pressure of less than 0.1 mm Hg. Still more preferably, the predetermined amount of carbon dioxide is as little as can be practically achieved. In this aspect, the bandage is preferably sealed to the environment until application of the bandage to prevent premature uptake of carbon dioxide from the environment.

In a presently preferred embodiment of the present invention, the perfluorochemical fluid is both saturated with dissolve oxygen and contains as little dissolved carbon dioxide as is practical. When the bandage is applied to the skin or wound, oxygen diffuses out of the reservoir through the membrane to the skin or wound, while carbon dioxide diffuses from the skin or wound through the membrane to dissolve in the perfluorochemical fluid in the reservoir.

The perfluorochemical fluid ("PFC") is preferably comprises at least one fluorinated hydrocarbon having at least one-half of the corresponding hydrocarbon's hydrogen atoms substituted by fluorine. More preferably, the perfluorochemical fluid is selected from the group consisting of $C_4F_9CH=CH_4C_9$, $i\text{-}C_3F_9CH=CHC_6F_{13}$, $C_6F_{13}CH=CHC_6F_{13}$, $C_{10}F_{18}$, $C_8F_{17}Br$, $C_8F_{16}O$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$-perfluorohexanes, FC-77, and mixtures thereof.

Oxygen and other gases such as carbon dioxide are known to be highly soluble in perfluorochemical fluids. In the present invention, it is preferred that the perfluorochemical fluid in the reservoir be pretreated and oxygenated to its fullest capacity. In some instances, this will be up to 300 times the volume of the perfluorochemical fluid, depending on the characteristics of some perfluorochemical fluid selected.

The size and shape of the reservoir, and the materials used for constructing the reservoir, depend upon the intended clinical application of the bandage.

The reservoir can optionally include a gel matrix or fibrous, woven or non-woven material to provide mechanical strength and structure to the reservoir.

The bottom of the reservoir is formed by a membrane permeable to oxygen to allow release of the oxygen across the membrane into tissue or skin. Preferably, the membrane is also permeable to carbon dioxide, to permit carbon dioxide to diffuse across the membrane form the tissue or skin to which the bandage is applied and to dissolve in the perfluorochemical fluid in the reservoir. The other reservoir walls are preferably not permeable to oxygen, or at least have a substantially lower permeability than the membrane.

The release of oxygen into the target skin or tissue is controlled by a number of factors, including the characteristics of the perfluorochemical fluid (such as the viscosity, vapor pressure, and gas solubility), the characteristics of the membrane, the surface area of application, the volume of perfluorochemical fluid and oxygen, as well as the temperature of the perfluorochemical fluid.

In addition to the perfluorochemical fluid and the dissolved oxygen, the reservoir can optionally contain medicaments such as pharmaceutical and/or biological agents (BA) and chemicals, including but not limited to tissue growth promoters, hormones, cytokines, vascularizing agents, receptors, ligands, antibodies, natural peptides, synthetic peptides, fusion proteins, antibiotics and other drugs, nucleic acids, encapsulated nucleic acids, autologous molecules, anti-inflammatory agents, genetic therapy delivery systems, intradermal penetration agents, and the like to promote tissue healing. In some cases, such medicaments can be dissolved in the perfluorochemical fluid. Alternatively, the medicament can be included, for example, in a coating layer on the outside of the membrane, or the membrane itself may include one or more such medicaments. Alternatively, the bandage can include a second reservoir positioned between the first reservoir and the bottom of the bandage. In this case the a first gas-permeable membrane separates the perfluorochemical fluid reservoir from the second reservoir, and a second membrane permeable to both gas, and in particular oxygen, and the medicament in the second reservoir forms a second wall of the second reservoir. When such medicaments are provided within the reservoir, the membrane should be selected to permit transmission of the medicament through the membrane from the reservoir to the skin or tissue.

Other gases can also be dissolved in the perfluorochemical fluid oxygen to improve tissue oxygenation in appropriate clinical settings. For instance, gases such as helium, nitric oxide, etc. can be included, with the goal of promoting better delivery and/or tissue perfusion, and thus oxygenation, of the tissue at the site to which the bandage is applied.

In some, but not all, clinical situations, charge application to skin or wounds is desirable. In such cases, the present invention provides for the application of charged particles to the skin or wound by the addition of charged particles to the perfluorochemical fluid combined with selection of a membrane permeable to the charged particles.

Permeable membranes are well known in the art. For example, permeable membranes can be formed from a variety of natural and synthetic polymers, including, for example, acrylates, polyurethanes, polysulfones, polyether sulfones, polyvinyl alcohols, polyvinyl chlorides, polyvinylidene fluorides, polytetrafluoroethylenes, cellulose acetate, alginates, chitosan, agar, and mixtures thereof. Any polymeric material having the desired permeability and sufficient mechanical strength to retain the perfluorochemical fluid within the reservoir can be employed.

Oxygen-permeable membranes can be prepared from a variety of polymeric materials including polytetrafluoroethylenes, polypropylenes, polystyrenes, polysulfones, and polyurethanes.

The cover can be formed from a synthetic polyester material, a polyolefin, or some other material that is substantially impermeable to the passage of oxygen. By "substantially impermeable" is meant having a gas permeability coefficient of less than about 1 Barrer ($10^{-10}$ $cm^3$(STP)cm/$cm^2$ sec cm Hg).

The adhesive layer can be formed from a suitable polyisobutylene, polysilicone, or polyacrylate, with polyisobutylene being preferred. Preferably, the adhesive material is highly permeable to oxygen and carbon dioxide. Preferably, the adhesive material is selected to retain adhesive strength under a wide variety of conditions, as may be encountered by a subject to whom the bandage of the present invention has been applied, including bathing, exercising, high and low temperatures, high and low humidity, and the like. The adhesive layer can be applied over the entire surface of the membrane, or in a pattern covering only enough of the surface to provide secure contact between the bandage and the skin or wound to which the bandage is applied.

Suitable release materials include siliconized polymeric films such as siliconized polyester films.

In another aspect, the present invention provides a treatment process comprising applying to the skin or tissue of an animal a bandage comprising a reservoir containing perfluorochemical fluid, the reservoir being sealed by a gas-permeable membrane, and thereafter maintaining contact between the bandage and the skin or tissue for a predetermined period of time. In one aspect of this process, the perfluorochemical fluid has at least one gaseous material dissolved therein. Preferably, the gaseous material is oxygen, and the process employs a bandage as described above. In another aspect of the process of the present invention, the perfluorochemical fluid initially contains less than a predetermined amount of carbon dioxide dissolved in the perfluorochemical fluid before application of the bandage to the skin. Preferably, the predetermined amount of carbon dioxide dissolved in the perfluorochemical fluid has a maximum partial pressure of 45 mm Hg, approximately the partial pressure of carbon dioxide in blood circulating in a mammal. More preferably, the predetermined amount of carbon dioxide dissolved in the perfluorochemical fluid has a partial pressure of less than 0.1 mm Hg. Still more preferably, the predetermined amount of carbon dioxide is as little as can be practically achieved. Preferably, the bandage is preferably sealed to the environment until application of the bandage to prevent premature uptake of carbon dioxide from the environment, and the process additionally comprises removing the seal to expose the membrane.

Optionally, in the present process the temperature of the bandage can be controlled to modulate the transfer of oxygen across the membrane for delivery to the skin or tissue. For example, the bandage can be warmed to a predetermined temperature above body temperature to increase diffusion of the oxygen through the membrane. Heating or cooling of the bandage thus serves to modulate oxygenation, allowing controlled oxygenation of the skin, transdermal oxygenation, and removal of emitted gases as discussed above.

Various modifications can be made in the details of the various embodiments of the processes, compositions and articles of the present invention, all within the scope and spirit of the invention and defined by the appended claims.

The invention claimed is:

1. A bandage for application to the skin of an animal to promote skin health, skin healing and tissue healing, the bandage comprising a reservoir containing perfluorochemical fluid, the reservoir having a top and a bottom, the top of the reservoir being sealed to the environment, the reservoir being sealed on the bottom by a gas-permeable membrane, the gas-permeable membrane being sealed to the environment with a releasable cover, the perfluorochemical fluid having at least one gaseous material dissolved therein, the at least one gaseous material comprising both oxygen and carbon dioxide, the perfluorochemical fluid containing less than a predetermined amount of carbon dioxide dissolved in the perfluorochemical fluid, the predetermined amount of carbon dioxide having a partial pressure of 0.1 mm Hg, the concentration of oxygen and carbon dioxide in the perfluorochemical fluid being selected so that when the bandage is applied to the skin, oxygen will diffuse across the membrane from the reservoir to the skin and carbon dioxide will diffuse across the membrane from the skin to the reservoir.

2. A bandage according to claim 1 wherein the gas-permeability of the membrane increases as a function of temperature.

3. A bandage according to claim 1 further comprising an oxygen-impermeable cover, the reservoir being sealed between the cover and the membrane.

4. A bandage according to claim 1 wherein the perfluorochemical fluid is selected from the group consisting of $C_4F_9CH=CH_4C_9$, i-$C_3F_9CH=CHC_6F_{13}$, $C_6F_{13}CH=CHC_6F_{13}$, $C_{10}F_{18}$, $C_8F_{17}Br$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$-perfluorohexanes, FC-77, and mixtures thereof.

5. A bandage according to claim 1 wherein the perfluorochemical fluid comprises at least one fluorinated hydrocarbon having at least one-half of the corresponding hydrocarbon's hydrogen atoms substituted by fluorine.

6. A bandage according to claim 1 further comprising dissolving other therapeutic gases in the perfluorochemical fluid to enhance the oxygenation of the perfluorochemical fluid.

7. A bandage according to claim 6 wherein other gases are selected from the group consisting of helium and nitric oxide.

8. A treatment process for promoting skin health, skin healing and tissue healing, the process comprising:
(a) applying to a site on the skin or wound of an animal a bandage comprising a reservoir containing perfluorochemical fluid, the reservoir having a top and a bottom, the top of the reservoir being sealed to the environment, the reservoir being sealed on the bottom by a gas-permeable membrane, the gas-permeable membrane being sealed to the environment with a releasable cover, the cover being released before applying the bandage to the skin, the perfluorochemical fluid having at least one gaseous material dissolved therein, the at least one gaseous material comprising both oxygen and carbon dioxide, the perfluorochemical fluid containing less than a predetermined amount of carbon dioxide dissolved in the perfluorochemical fluid, the predetermined amount of carbon dioxide having a partial pressure of 0.1 mm Hg, the concentration of oxygen and carbon dioxide in the perfluorochemical fluid being selected so that when the bandage is applied to the skin, oxygen will diffuse across the membrane from the reservoir to the skin and carbon dioxide will diffuse across the membrane from the skin to the reservoir, and
(b) maintaining contact between the bandage and the skin for a predetermined period of time, the bandage functioning to oxygenate the site and to remove carbon dioxide from the site to which the bandage is applied.

9. A treatment process according to claim 8 wherein the bandage comprises a removable seal covering the membrane, and additionally comprising removing the seal before applying the bandage to the skin.

10. A treatment process according to claim 8 wherein the permeability of the membrane to the gaseous material increases as a function of temperature.

11. A treatment process according to claim 8 wherein the bandage further comprises an oxygen-impermeable cover, the reservoir being sealed between the cover and the membrane.

12. A treatment process according to claim 8 wherein the perfluorochemical fluid is selected from the group consisting of $C_4F_9CH=CH_4C_9$, i-$C_3F_9CH=CHC_6F_{13}$, $C_6F_{13}CH=CHC_6F_{13}$, $C_{10}F_{18}$, $C_8F_{17}Br$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$-perfluorohexanes, FC-77, and mixtures thereof.

13. A treatment process according to claim 8 further comprising dissolving other therapeutic gases in the perfluorochemical fluid to enhance the oxygenation of the perfluorochemical fluid.

14. A treatment process according to claim 13 wherein other gases are selected from the group consisting of helium and nitric oxide.

15. A bandage according to claim 1 wherein the predetermined amount of carbon dioxide is as little as can be practically achieved.

16. A treatment process according to claim 8 wherein the predetermined amount of carbon dioxide is as little as can be practically achieved.

* * * * *